United States Patent [19]

Sikkenga

[11] 4,435,311

[45] Mar. 6, 1984

[54] CONTINUOUS REACTIVATION OF AMS-1B-CONTAINING CATALYST SYSTEMS

[75] Inventor: David L. Sikkenga, Wheaton, Ill.

[73] Assignee: Standard Oil Company (Indiana), Chicago, Ill.

[21] Appl. No.: 422,745

[22] Filed: Sep. 24, 1982

[51] Int. Cl.³ .............................................. B01J 37/10
[52] U.S. Cl. .................................... 502/22; 585/660; 502/34; 502/53; 502/85
[58] Field of Search .................. 252/420, 432; 585/660

[56] References Cited

U.S. PATENT DOCUMENTS

| | | | |
|---|---|---|---|
| 4,049,573 | 9/1977 | Kaeding | 252/432 |
| 4,070,272 | 1/1978 | Rausch | 252/432 |
| 4,305,842 | 12/1981 | Asakawa et al. | 252/432 |

Primary Examiner—Delbert E. Gantz
Assistant Examiner—Anthony McFarlane
Attorney, Agent, or Firm—Wallace L. Oliver; William T. McClain; William H. Magidson

[57] ABSTRACT

A process to reactivate a noble metal-containing AMS-1B crystalline borosilicate catalyst comprising contacting such catalyst with water.

18 Claims, 2 Drawing Figures

4,435,311

CONTINUOUS REACTIVATION OF AMS-1B-CONTAINING CATALYST SYSTEMS

BACKGROUND OF THE INVENTION

This invention relates to reactivating partially deactivated catalysts and more particularly relates to reactivating partially deactivated catalysts based on AMS-1B crystalline borosilicate molecular sieve containing a noble metal.

Commonly assigned U.S. patent application Ser. No. 422,821 filed Sept. 24, 1982, incorporated by reference herein, disclosed conversion of normal alkanes, such as n-butane, to more useful products such as isobutylene. The catalyst used in such conversion was based on AMS-1B crystalline borosilicate molecular sieve containing a noble metal. This catalyst, similar to essentially all heterogeneous catalysts, deactivates over time. The conventional method of reactivating such catalysts is to pass oxygen through a catalyst bed of a hydrocarbon conversion unit to burn accumulations of coke. During such oxygen regeneration hydrocarbon conversion is interrupted. A method of regenerating a catalyst without requiring a costly shutdown would be advantageous. The invention described herein is a method of onstream regeneration of a partially deactivated catalyst by addition of water. Use of small amounts of water to affect product composition in alkyl aromatic isomerization using an AMS-1B crystalline borosilicate molecular sieve catalyst was disclosed in commonly assigned U.S. patent application Ser. No. 281,730 filed July 9, 1981. However, the effect of regeneration of a partially deactivated catalyst using AMS-1B crystalline borosilicate containing a noble metal was not disclosed therein. Also commonly assigned U.S. patent applications Ser. Nos. 422,743,422,822,422,742,422,744 all filed Sept. 24, 1982 all incorporated by reference herein, disclose conversion of various alkenes under various conditions using a catalyst based on AMS-1B crystalline borosilicate.

Zeolitic materials, both natural and synthetic, are known to have catalytic capabilities for many hydrocarbon processes. Zeolitic materials typically are ordered porous crystalline aluminosilicates having a definite structure with cavities interconnected by channels. The cavities and channels throughout the crystalline material generally are uniform in size allowing selective separation of hydrocarbons. Consequently, these materials in many instances are known in the art as "molecular sieves" and are used, in addition to selective adsorptive processes, for certain catalytic properties. The catalytic properties of these materials are affected to some extent by the size of the molecules which selectively penetrate the crystal structure, presumably to contact active catalytic sites within the ordered structure of these materials.

Generally, the term "molecular sieve" includes a wide variety of both natural and synthetic positive-ion-containing crystalline zeolite materials. They generally are characterized as crystalline aluminosilicates which comprise networks of $SiO_4$ and $AlO_4$ tetrahedra in which silicon and aluminum atoms are cross-linked by sharing of oxygen atoms. The negative framework charge resulting from substitution of an aluminum atom for a silicon atom is balanced by positive ions, for example, alkali-metal or alkaline-earth-metal cations, ammonium ions, or hydrogen ions.

Prior art developments have resulted in formation of many synthetic zeolitic crystalline materials. Crystalline aluminosilicates are the most prevalent and, as described in the patent literature and in the published journals, are designated by letters or other convenient symbols. Examples of these materials are Zeolite A (U.S. Pat. No. 2,882,243), Zeolite X (U.S. Pat. No. 2,882,244), Zeolote Y (U.S. Pat. No. 3,130,007), Zeolite ZSM-4 (U.S. Pat. No. 3,578,723), Zeolite ZSM-5 (U.S. Pat. No. 3,702,886), Zeolite ZSM-11 (U.S. Pat. No. 3,709,979), Zeolite ZSM-12 (U.S. Pat. No. 3,832,449), Zeolite NU-1 (U.S. Pat. No. 4,060,590) and others.

Boron is not considered a replacement for aluminum or silicon in a zeolitic composition. However, recently a new crystalline borosilicate molecular sieve AMS-1 B with distinctive properties was disclosed in U.S. Pat. Nos. 4,268,420 and 4,269,813 incorporated by reference herein. According to these patents AMS-1 B can be synthesized by crystallizing a source of an oxide of silicon, an oxide of boron, an oxide of sodium and an organic template compound such as a tetra-n-propylammonium salt. The process of this invention uses AMS-1 B crystalline borosilicate molecular sieve.

Hydrocarbon conversion processes are known using othe zeolitic materials. Examples of such processes are dewaxing of oil stock (U.S. Pat. Nos. 3,852,189, 4,211,635 and Reissue No. 28,398); conversion of lower olefins (U.S. Pat. Nos. 3,965,205 and 3,960,978 and European patent application No. 31,675); aromatization of olefins and aliphatics (U.S. Pat. Nos. 3,761,389, 3,813,330, 3,827,867, 3,827,868, 3,843,740, 3,843,741 and 3,914,171); hydrocracking and oligomerization of hydrocabons (U.S. Pat. Nos. 3,753,891, 3,767,568, 3,770,614 and 4,032,432); conversion of ethane to aromatics and $C_3+$ hydrocarbons (U.S. Pat. No. 4,100,218); conversion of straight-chain and slightly branched-chain hydrocarbons to olefins (U.S. Pat. Nos. 4,309,275 and 4,309,276); and conversion of $C_4$ paraffins to aromatics (U.S. Pat. No. 4,291,182).

A method to reactivate a catalyst system containing AMS-1 B crystalline borosilicate would be desirable and a method to reactivate such catalyst in a continuous manner during hydrocarbon conversion would be very advantageous.

SUMMARY OF THE INVENTION

Figure 1:
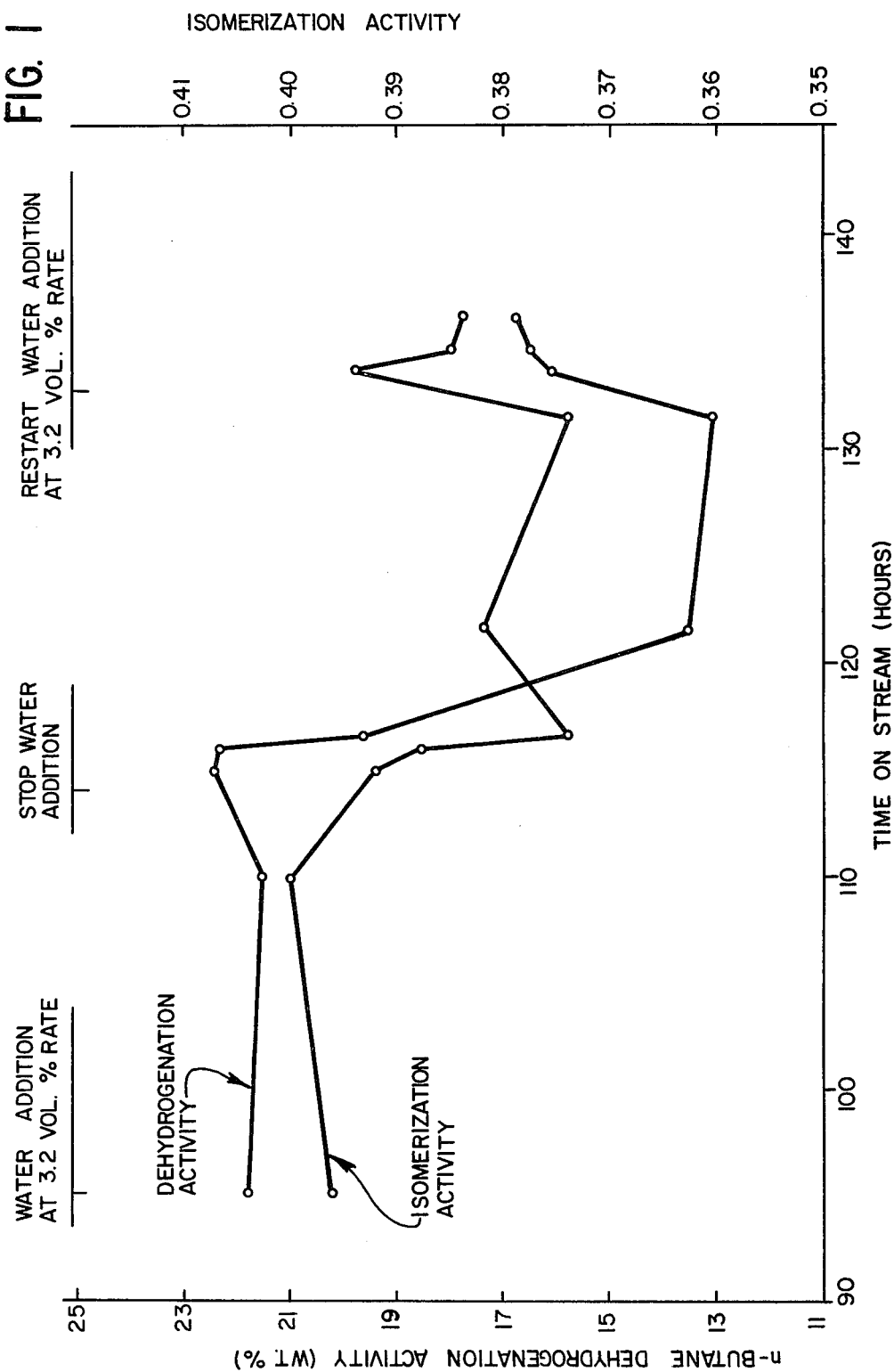
FIG. 1 illustrates data obtained in Example I and shows the catalyst reactivation effect of water vapor addition to n-butane isomerization and dehydrogenation over an AMS-1 B crystalline borosilicate catalyst containing a noble metal.
Figure 2:
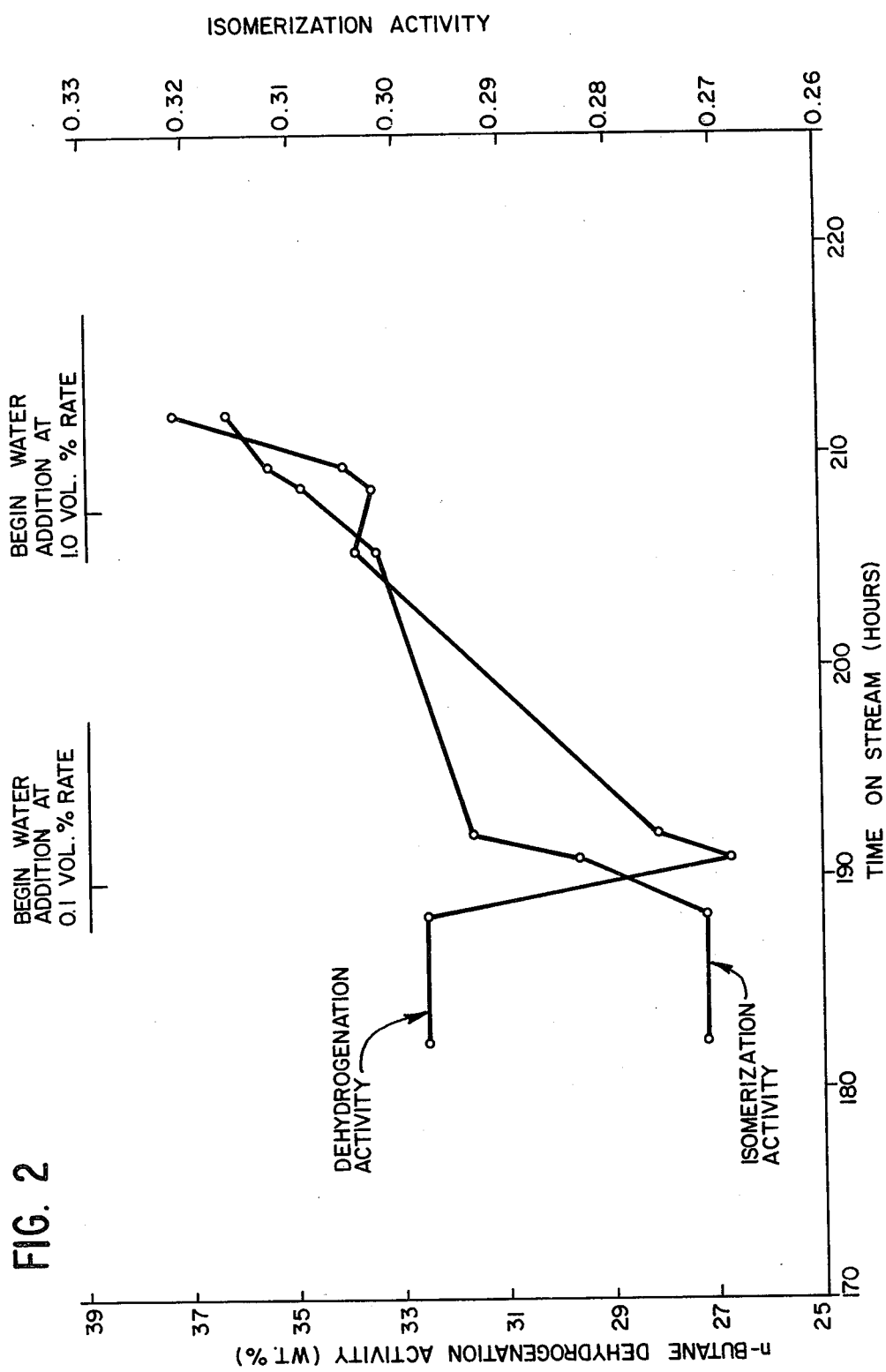
FIG. 2 illustrates data obtained in Example II and shows the catalyst reactivation effect of water vapor addition to a noble metal-containing AMS-1 Bcrystalline borosilicate catalyst system.

A process to reactivate a noble metal-containing AMS-1 B crystalline borosilicate catalyst comprises contacting such catalyst with water.

BRIEF DESCRIPTION OF THE INVENTION

This invention is a method to reactivate a catalyst system based on AMS-1 B crystalline borosilicate containing a noble metal. Such systems are useful in converting a linear alkane, such as n-butane, to dehydrogenated and isomerized products such as normal butenes and isobutylene. Also noble metal-containing AMS-1B crystalline borosilicate catalysts are useful in converting alkenes such as propylene and normal butenes by isomerization, oligimerization and aromatization. Details of such processes are described in the above-indicated commonly assigned U.S. patent applications.

In the method of this invention a noble metal-containing AMS-1B crystalline borosilicate catalyst system is reactivated by contact with water. Water vapor in a carrier gas is contacted with such AMS-1B-containing catalyst at concentrations of about 0.01 to about 20 vol.%, and typically ranges from 0.1 to about 5 vol.%. The carrier gas may be hydrogen, an inert gas, such as nitrogen or helium, or a hydrocarbon such as an alkane or alkene. Examples of suitable carrier gases include methane, ethylene, ethane, propane, propylene, butanes, butenes, pentanes, pentenes and the like. The carrier gas can be any gas compatible with the reaction system. In conversion of an alkane, such as n-butane, the carrier gas for the reactivation water vapor preferably is the n-butane feedstream.

It is contemplated that catalyst reactivation can occur using the method of this invention in a continuous or substantially continuous manner by incorporation of water vapor into a hydrocarboncontaining feedstream during hydrocarbon conversion. Alternative methods include sporatic or intermittent contact of catalyst with water vapor during or not during hydrocarbon conversion. The preferable mode, however, is a substantially continuous contact of water vapor with the AMS-1B-containing catalyst during hydrocarbon conversion.

Reactivation of an AMS-1B-containing catalyst according to this invention is performed by contacting a gas stream containing water vapor with the catalyst. Typically, reactivation conditions are those used in hydrocarbon conversion using the same catalyst system and include temperatures of about 100° to 750° C. at pressure of about 0.1 to about 100 atmospheres (10 to 10,000 kPa). In a typical reactivation process the temperature can be about 400° to about 650° C. and the pressure can be about 0.2 to about 10 atmospheres (20 to 1000 kPa). In a preferable process in which n-butane is converted during reactivation the temperature can be about 500° to about 650° C. and the pressure can be about 0.3 to about 3 atmospheres (30 to 300 kPa).

Alkanes which can be converted during the reactivation process of this invention include alkanes containing up to about 10 carbon atoms and include linear alkanes such as ethane, propane, n-butane, n-pentane, n-hexane, n-heptane, n-octane, n-nonane and n-decane and isoalkanes such as isobutane, 2-methylbutane, 2-methylpentane, 2-methylhexane and the like.

Preferable alkanes useful in this invention are linear alkanes and isoalkanes having three to six carbon atoms. Preferable alkanes useful in this invention include n-butane and isobutane. Mixtures of alkanes can be used in the process of this invention.

Similiarly, alkenes can be converted during the catalyst reactivation process of this invention. Suitable alkenes contain up to about 10 carbon atoms and, typically, are normal alkenes such as propylene and n-butenes. Normal butenes include 1-butene, trans-2-butene and cis-2-butene.

The hydrocarbons or mixtures thereof, used in the process of this invention can be in the presence of other substances such as other hydrocarbon-based molecules. For example, a feedstream used in the process of this invention comprising a linear alkane also can contain other hydrocarbons such as alkenes, methane, aromatics, hydrogen, and inert gases. A process in which partially reacted hydrocarbons are recycled will contain a mixture including alkanes, alkenes, methane and aromatics. Typically, a linear alkane feedstream used in this invention contains about 10 to 100 wt.% linear alkane and preferably contains about 50 to 100 wt.% linear alkane. A typical mixture of n-butane and n-butenes useful in this invention comprises about 80 wt.% n-butane and about 20wt.% n-butenes.

The catalyst useful in this invention is based on the crystalline borosilicate molecular sieve, AMS-1B, described in U.S. Pat. Nos. 4,268,420 and 4,269,813, incorporated herein by reference. A particularly useful catalyst for this invention contains AMS-1B in which a noble metal is placed by ion exchange, impregnation or other means.

The catalyst system which is useful in this invention comprises a borosilicate catalyst system based on a molecular sieve material identified as AMS-1B. Details as to the preparation of AMS-1B are described in U.S. Pat. No. 4,269,813. Such AMS-1B crystalline borosilicate generally can be characterized by the X-ray pattern listed in Table I and by the composition formula:

$$0.9\pm0.2 M_{2/n}O:B_2O_3:ySiO_2:zH_2O$$

wherein M is at least one cation, n is the valence of the cation, y is between 4 and about 600 and z is between 0 and about 160.

TABLE I

| d-Spacing Å (1) | Assigned Strength (2) |
|---|---|
| 11.2 ± 0.2 | W-VS |
| 10.0 ± 0.2 | W-MS |
| 5.97 ± 0.07 | W-M |
| 3.82 ± 0.05 | VS |
| 3.70 ± 0.05 | MS |
| 3.62 ± 0.05 | M-MS |
| 2.97 ± 0.02 | W-M |
| 1.99 ± 0.02 | VW-M |

(1) Copper K alpha radiation
(2) VW = very weak; W = weak; M = medium; MS = medium strong; VS = very strong The AMS-1B borosilicate molecular sieve useful in this invention can be prepared by crystallizing an aqueous mixture, at a controlled pH, of sources for cations, an oxide of boron, an oxide of silicon, and an organic template compound.

Typically, the mole ratios of the various reactants can be varied to produce the crystalline borosilicates of this invention. Specifically, the mole ratios of the initial reactant concentrations are indicated below:

|  | Broad | Preferred | Most Preferred |
|---|---|---|---|
| $SiO_2/B_2O_3$ | 5-400 | 10-150 | 10-80 |
| $R_2O^+/[R_2O^+ + M_{2/n}O]$  | 0.1-1.0 | 0.2-0.97 | 0.3-0.97 |
| $OH^-/SiO_2$ | 0.01 | 0.1-2 | 0.1-1 |
| $H_2O/OH^-$ | 10-4000 | 10-500 | 10-500 | wherein R is an organic compound and M is at least one cation having a valence n, such as an alkali metal or an alkaline earth metal cation. By regulation of the quantity of boron (represented as $B_2O_3$) in the reaction mixture, it is possible to vary the $SiO_2/B_2O_3$ molar ratio in the final product.

More specifically, the material useful in the present invention is prepared by mixing a cation source compound, a boron oxide source, and an organic template compound in water (preferably distilled or dionized). The order of addition usually is not critical although a typical procedure is to dissolve sodium hydroxide and boric acid in water and then add the template compound. Generally, after adjusting the pH, the silicon oxide compound is added with intensive mixing such as that performed in a Waring Blender. After the pH is checked and adjusted, if necessary, the resulting slurry is transferred to a closed crystallization vessel for a suitable time. After crystallization, the resulting crystalline product can be filtered, washed with water, dried, and calcined.

During preparation, acidic conditions should be avoided. When alkali metal hydroxides are used, the values of the ratio of $OH^-/SiO_2$ shown above should furnish a pH of the system that broadly falls within the range of about 9 to about 13.5. Advantageously, the pH of the reaction system falls within the range of about 10.5 to about 11.5 and most preferably between about 10.8 and about 11.2.

Examples of oxides of silicon useful in this invention include silicic acid, sodium sliicate, tetraalkyl silicates and Ludox, a stabilized polymer of silicic acid manufactured by E. I. du Pont de Nemours & Co. Typically, the oxide of boron source is boric acid although equivalent species can be used such as sodium borate and other boron-containing compounds.

Cations useful in formation of AMS-1B include alkali metal and alkaline earth metal cations such as sodium, potassium, lithium, calcium and magnesium. Ammonium cations may be used alone or in conjunction with such metal cations. Since basic conditions are required for crystallization of the molecular sieve of this invention, the source of such cation usually is a hydroxide such as sodium hydroxide. Alternatively, AMS-1B can be prepared directly in the hydrogen form by replacing such metal cation hydroxides with an organic base such as ethylenediamine.

Organic templates useful in preparing AMS-1B crystalline borosilicate include alkylammonium cations or precursors thereof such as tetraalkylammonium compounds. A useful organic template is tetra-n-propylammonium bromide. Diamines such as hexamethylenediamine, can be used.

In a more detailed description of a typical preparation of this invention, suitable quantities of sodium hydroxide and boric acid ($H_3BO_3$) are dissolved in distilled or deionized water followed by addition of the organic template. The pH may be adjusted between about $11.0 \pm 0.2$ using a compatible base or acid such as sodium bisulfate or sodium hydroxide. After sufficient quantities of silicic acid polymer (Ludox) are added with intensive mixing, preferably the pH is again checked and adjusted to a range of about $11.0 \pm 0.2$. The resulting slurry is transferred to a closed crystallization vessel and reacted usually at a pressure at least the vapor pressure of water for a time sufficient to permit crystallization which usually is about 0.25 to about 20 days, typically is about one to about ten days and preferably is about five to about seven days, at a temperature ranging from about 100° to about 250° C., preferably about 125° to about 200° C. The crystallizing material can be stirred or agitated as in a rocker bomb. Preferably, the crystallization temperature is maintained below the decomposition temperature of the organic template compound. Especially preferred conditions are crystallizing at about 165° C. for about five to about seven days. Samples of material can be removed during crystallization to check the degree of crystallization and determine the optimum crystallization time.

The crystalline material formed can be separated and recovered by well-known means such as filtration with washing. This material can be mildly dried for anywhere from a few hours to a few days at varying temperatures, typically about 25°-200° C., to form a dry cake which can then be crushed to a powder or to small particles and extruded, pelletized, or made into forms suitable for its intended use. Typically, materials prepared after mild drying contain the organic template compound and water of hydration within the solid mass and a subsequent activation or calcination procedure is necessary, if it is desired to remove this material from the final product. Typically, mildly dried product is calcined at temperatures ranging from about 260° to about 850° C. and preferably about 525° to about 600° C. Extreme calcination temperatures or prolonged crystallization times may prove detrimental to the crystal structure or may totally destroy it. Generally there is no need to raise the calcination temperature beyond about 600° C. in order to remove organic material from the originally formed crystalline material. Typically, the molecular sieve material is dried in a forced draft oven at 165° C. for about 16 hours and is then calcined in air in a manner such that the temperature rise does not exceed 125° C. per hours until a temperature of about 540° C. is reached. Calcination at this temperature usually is continued for about 4 to 16 hours.

A catalytically active material can be placed onto the borosilicate structure by ion exchange, active metal ion or compound on the borosilicate structure, the borosilicate may be in the hydrogen form which, typically, is produced by exchange one or more times with ammonium ion, typically using ammonium acetate, followed by drying and calcination as described above.

The original cation in the AMS-1B crystalline borosilicate, which usually is sodium ion, can be replaced all or in part by ion exchange with other cations including other metal ions and their amine complexes, alkylammonium ions, ammonium ions, hydrogen ions, and mixtures thereof. Preferred replacing cations are those which render the crystalline borosilicate catalytically active, especially for hydrocarbon conversion. Typically catalytically active ions include hydrogen, metal ions of Groups IB, IIA, IIB, IIIA, VB, VIB and VIII, and of manganese, vanadium, chromium, uranium, and rare earth elements.

Also, water soluble salts of catalytically active materials can be impregnated onto the crystalline borosilicate of this invention. Such catalytically active materials include metals of Groups IB, IIA, IIB, IIIA, IIIB, IVB, VB, VIB, VIIB, and VIII, and rare earth elements.

Catalyst compositions useful in this invention preferably contain Group VIII elements while most preferably noble metals are used in this invention as catalytically active material. Such noble metals include ruthenium, osmium, rhodium, iridium, palladium and platinum; platinum and palladium are preferable while platinum is the most preferable. Mixtures of noble metals can be used.

In addition, preferable catalyst compositions are prepared containing a noble metal in combination with another metal ion or compound including Groups IB, IIB, IIIB, IVB, VB, VIB, VIIB and VIII metals and rare earth elements. Specific additional catalytic materials include ions and compounds of copper, lanthanum, molybdenum, cobalt, tungsten and nickel. Other additional catalytic materials can be ions and compounds of scandium, yttrium, titanium, zirconium, hafnium, vanadium, niobium, tantalum, chromium, cerium, manganese, iron, zinc and cadmium. Specific combinations of noble metal and other catalytic materials include ions or compounds of platinum and copper, platinum and lanthanum, platinum and cobalt, platinum and nickel, platinum and molybdenum, and platinum and tungsten.

Ion exchange and impregnation techniques are well-known in the art. Typically, an aqueous solution of a cationic species is exchanged one or more times at about 25° to about 100° C. A hydrocarbonsoluble metal compound such as a metal carbonyl also can be used to place a catalytically active material. Impregnation of a catalytically active compound on the borosilicate or on a composition comprising the crystalline borosilicate suspended in and distributed throughout a matrix of a support material, such as a porous refractory inorganic oxide such as alumina, often results in a suitable catalytic composition. A combinatin of ion exchange and impregnation can be usd. Presence of sodium ion in a composition usually is detrimental to catalytic activity.

The amount of catalytically active material placed on the AMS-1B crystalline borosilicate can vary from about 0.01 weight percent to about thirty weight percent, typically from about 0.05 to about 25 weight percent, depending on the process use intended. The optimum amount can be determined easily by routine experimentation.

The AMS-1B crystalline borosilicate useful in this invention may be used as a pure material in a catalyst or may be admixed with or incorporated within various binders or matrix materials depending upon the intended process use. The crystalline borosilicate can be combined with active or inactive materials, synthetic or naturally-occurring zeolites, as well as inorganic or organic materials which would be useful for binding the borosilicate. Wellknown materials include silica, silica-alumina, alumina, magnesia, titania, zirconia, alumina sols, hydrated aluminas, clays such as bentonite or kaolin, or other binders well known in the art. Typically, the borosilicate is incorporated within a matrix material by blending with a sol of the matrix material and gelling the resulting mixture. Also, solid particles of the borosilicate and matrix materialcan be physically admixed. Typically, such borosilicate compositions can be pelletized or extruded into useful shapes. The crystalline borosilicate content can vary anywhere from a few up to 100 wt.% of the total composition. Catalytic compositions can contain about 0.1 wt.% to about 100 wt.% crystalline borosilicate material and preferably contain about 10 wt.% to about 95 wt.% of such material and most preferably contain about 40 wt.% to about 80 wt.% of such material.

Catalytic compositions comprising th crystalline borosilicate material of this invention and a suitable matrix material can be formed by adding a finely-divided crystalline borosilicate and a catalytically active metal compound to an aqueous sol or gel of the matrix material. The resulting mixture is thoroughly blended and gelled typically by adding a material such as ammonium hydroxide. The resulting gel can be dried and calcined to form a composition in which the crystalline borosilicate and catalytically active metal compound are distributed throughout the matrix material.

Specific details of catalyst preparations are described in U.S. Pat. No. 4,269,813.

In a process using this invention, a stream of a hydrocarbon, such as n-butane, is contacted with a catalytic material-containing AMS-1B borosilicatebased catalyst. Generally, in a preferable process of this invention an alkane such as a linear alkane or an isoalkane is contacted with the above-described AMS-1B borosilicate-based catalyst system in the luqiid or vapor phase at a suitable reaction temperature, pressure and space velocity. Generally, suitable reaction conditions include a temperature of about 100° to about 750° C., a pressure of about 0.1 to about 100 atmospheres (10 to 10,000 kPa) or higher with hydrogen/hydrocarbon ratio of 0 to about 10 or higher at weight hourly space velocity (WHSV) of about 0.1 to about 40 $hr^{-1}$. In a typical process scheme, an n-butane-containing hydrocarbon stream is contacted with such catalyst in a reactor at about 400° to about 650° C. at a pressure of about 0.2 to about 10 atmospheres (20 to 1000 kPa) with a hydrogen/butane ratio of 0 to about 10 at a WHSV of about 0.3 to about 25 $hr^{-1}$. Preferably the n-butane conversion process of this invention is conducted at about 500° to about 600° C. at a pressure of about 0.3 to about 3 atmospheres (30 to 300 kPa) with a hydrogen/butane molar ratio of about 0.5 to about 6 at a WHSV of about 1 to about 6 $hr^{-1}$.

Although conversion of n-butane is the preferable process of this invention, propane, ethane and isobutane similarly can be converted to propylene, ethylene and isobutylene although more severe conditions (higher temperature and pressures and lower space velocities) typically are used for ethane and propane. For conversion of ethane and propane preferable conditions are temperatures at about 500° to about 650° C., space velocities of about 0.1 to about 25 $hr^{-1}$ and pressures of about 0.2 to about 1 atmosphere (20 to 100 kPa).

The hydrocarbon feed useful in this invention comprises an alkane or alkene containing 2 to about 10 carbon atoms. The preferable feed contains predominantly $C_4$ hydrocarbons although typically minor amounts of other hydrocarbon components may be present. The hydrocarbon feedstream may be diluted with an inert gas such as nitrogen or helium. A typical butane-rich feedstream contains about 80 wt.% n-butane and about 20 wt.% n-butenes and isobutane.

As illustrated in the Figures, water addition to a noble metal-containing AMS-1B crystalline borosilicate catalyst during hydrocarbon conversion reactivates catalyst activity.

This invention is demonstrated but not limited by the following Examples.

EXAMPLE I

A catalyst composition was prepared by blending a mixture of 14.3 grams of hydrogen-form AMS-1B (containing 0.44 wt. % boron), 29.8 grams PHF alumina sol (containing 9.55 wt. % solids) and 16.0 milliliters of distilled water for 10 minutes followed by addition of two milliliters of an aqueous solution containing 0.0327 grams of $Pt(NH_3)_4Cl \cdot H_2O$ and further blending for three minutes.

The mixture was transferred to a glass dish and four grams of $NH_4OH$ (29% $NH_3$) was added to gel the mixture followed by mechanical stirring until the gel had a pasty texture. The gel was then dried at 150° C. for four hours and calcined at 300° C. After cooling to room temperature the solid mass was crushed and sieved to yield particles of 0.0164 to 0.0278-inch diameter.

A 1.88-grams sample of the above catalyst was supported in a 0.4-inch (ID) reactor by stainless steel helicies. After reduction of the catalyst in flowing hydrogen for one hour at 493° C, the catalyst was sulfided with 1.2 liters of 0.8 percent hydrogen sulfide in hydrogen over a five-minute period.

Following the sulfiding various mixtures of hydrogen, butane and water were passed over the catalyst. Hydrogen (15 liters/hr) and n-butane (11 grams/hour) were introduced into the reactor which was maintained at 538° C. at one atmosphere pressure. During the conversion reaction, samples of product were removed from the reactor and analyzed by gas chromatography. Water was added to the reactor at a rate of 3.2 vol.% at times during the experiment. Results of n-butane conversion with and without water addition are listed in Table II and illustrated in FIG. 1. The results show that samples taken at 95 and 109.8 hours on stream indicate that the catalyst is lined out with little change occurring over a 15-hour period. However, as soon as the water injection is stopped, both dehydrogenation activity (n-butane conversion) and isomerization activity (measured by the isobutylene/total butylene ratio) decreased. Restarting water injection, however, rapidly increases by dehydrogenation and isomerization activities. These results indicate that the presence of water in the reactor both maintains catalytic activity and reactivates a deactivated catalyst.

TABLE II

| Time on Stream (hours) | Water Addition Rate to Reactor (vol. %) | n-Butane Conversion (1) | Isobutylene to $C_4$ Olefins Ratio (2) | Selectivity to $C_4$'s (3) |
|---|---|---|---|---|
| 95 | 3.2 | 21.8 | 0.396 | 83.0 |
| 109.8 | 3.2 | 21.5 | 0.400 | 83.2 |
| 113.8 | 0 | | 0.392 | 81.4 |
| 114.8 | 0 | 22.4 | 0.388 | 82.7 |
| 115.8 | 0 | 22.5 | 0.374 | 86.5 |
| 116.8 | 0 | 19.6 | 0.382 | 89.0 |
| 121.5 | 0 | 13.9 | 0.374 | 89.5 |
| 131.3 | 0 | 13.1 | 0.394 | 86.4 |
| 132.5 | 3.2 | | 0.385 | 86.6 |
| 133.5 | 3.2 | 16.3 | 0.384 | 85.5 |
| 134.5 | 3.2 | 17.5 | | |
| 136.5 | 3.2 | 17.8 | | |

(1) Weight percent of n-butane converted indicating dehydrogenation activity.
(2) Weight ratio of isobutylene to total butylenes in reactor effluent indicating isomerization activity (thermodynamic equilibrium ratio is 0.446).
(3) Weight of $C_4$ hydrocarbons produced divided by weight of n-butane converted multiplied by 100.

EXAMPLE II

A catalyst composition was prepared by blending a mixture of 22.4 grams of uncalcined, sodium-three AMS-1B crystalline borosilicate (containing 0.8 wt. % boron) made using ethylenediamine as a base and tetrapropylammonium bromide as a template as described in commonly assigned U.S. patent application Ser. No. 279,207 filed June 30, 1981, 52.4 grams of PHF alumina sol (containing 9.55 wt. % solids) and 10.0 milliliters of distilled water.

After blending for five minutes, the mixture was transferred to a glass dish and 6.0 grams of $NH_4OH$ (29% $NH_3$) was added followed by stirring until a pasty texture was obtained. The material was dried in air at 150° C. for 18 hours, cooled, and crushed and sieved to yield particles of 0.0164 to 0.0278-inch diameter.

A 9.0-gram sample of the sized particles was contacted with 9 milliliters of a solution containing 0.163 gram $Pt(NH_3)_4Cl_2 \cdot H_2O$ and stirred until all catalyst particles appeared to be wetted uniformly. The platinum impregnated catalyst was then dried at 150° C. for four hours and calcined for four hours at 300° C. A 1.88-gram sample of the resultant catalyst was supported in a 0.4 inch (I.D.) stainless steel reactor by stainless steel helicies. Following reduction with flowing hydrogen at 493° C., mixtures of n-butane and hydrogen were passed over the catalyst at various temperatures and pressures. During the conversion reaction, samples of product were removed from the reactor and analyzed by gas chromatography. The samples were all taken at a reactor temperature of 535° C., 1 atmosphere and a hydrogen to butane ratio in the feed of 3.6-3.9. Water was added at times during the experiment.

Results of n-butane conversion with and without water addition are listed in Table III and illustrated in FIG. II. The results show that samples taken at 182.1 and 188.5 hours on stream illustrate that the partially deactivated catalyst is lined out with little change occurring over a 6-hour period. Addition of water to the feed to yield 0.1 volume percent water (vapor phase) resulted in an immediate increase in the isomerization activity as measured by the ratio of isobutylene to total $C_4$ olefins. Furthermore, after a temporary decline, the dehydrogenation activity (as measured by n-butane conversion) increased to above the level obtained prior to water addition. A ten-fold increase in water addition rate further increased both the dehydrogenation and isomerization activities of the catalyst.

TABLE III

| Time on Stream (hours) | Water Addition Rate to Reactor (vol. %) | n-Butane Conversion (1) | Isomerization Activity (2) | Selectivity to $C_4$'s (3) |
|---|---|---|---|---|
| 182.1 | 0 | 32.6 | 0.271 | 88.5 |
| 188.5 | 0 | 32.6 | 0.271 | 86.5 |
| 189.7 | 0.1 | | 0.283 | 93.9 |
| 190.7 | 0.1 | 26.7 | 0.293 | 94.6 |
| 191.8 | 0.1 | 28.1 | 0.302 | 86.4 |
| 205.3 | 0.1 | 33.8 | 0.309 | 87.9 |
| 207.3 | 1.0 | | 0.312 | 84.6 |
| 208.3 | 1.0 | 33.5 | 0.316 | 80.4 |
| 209.3 | 1.0 | 35.0 | | |
| 211.8 | 1.0 | 37.2 | | |

(1) Weight percent of n-butane converted indicating dehydrogenation activity.
(2) Weight ratio of isobutylene to total butylenes in reactor effluent indicating isomerization activity (thermodynamic equilibrium ratio is 0.446).
(3) Weight of $C_4$ hydrocarbons produced divided by weight of n-butane converted multiplied by 100.

What is claimed is:

1. A process to reactivate a noble metal-containing AMS-1B crystalline borosilicate comprising contacting such catalyst with water at reactivation conditions comprising a temperature of about 100° to about 750° C., a pressure of about 0.1 to about 100 atmospheres and a weight hourly space velocity of about 0.1 to about 40 $hr^{-1}$.

2. The process of claim 1 wherein the AMS-1B crystalline borosilicate catalyst is contacted with water vapor in a compatible carrier gas.

3. The process of claim 2 wherein the carrier gas is hydrogen, nitrogen, helium or a hydrocarbon.

4. The process of claim 1 wherein the noble metal is platinum or palladium.

5. The process of claim 1 wherein the noble metal is platinum.

6. The process of claim 1 wherein a hydrocarbon is converted during reactivation.

7. The process of claim 6 wherein the hydrocarbon is an alkane or alkene having up to about 10 carbon atoms.

8. The process of claim 6 wherein the hydrocarbon is ethane, propane, n-butane, isobutane, or normal butene or a mixture thereof.

9. The process of claim 6 wherein the hydrocarbon predominantly is a $C_4$ hydrocarbon.

10. The process of claim 6 wherein the hydrocarbon substantially is n-butane or isobutane.

11. The process of claim 2 wherein water vapor comprises from about 0.01 to about 20 vol. % of total vapor contacting the catalyst.

12. The process of claim 11 wherein water vapor comprises about 0.1 to about 5 vol.% of total vapor contacting the catalyst.

13. The process of claim 1 wherein the AMS-1B crystalline borosilicate composition is incorporated within an alumina, silica or silica-alumina matrix.

14. The process of claim 13 wherein the AMS-1B crystalline borosilicate content in the matrix ranges from about 10 to about 95 wt. %.

15. The process of claim 14 wherein the AMS-1B crystalline borosilicate content in the matrix ranges from about 40 to about 80 wt.%.

16. The process of claim 6 wherein hydrocarbon is converted at about 400° to about 650° C. at a pressure of about 0.2 to about 10 atmospheres with a hydrogen/butane ratio of 0 to about 10 at a weight hourly space velocity of about 0.1 to about 25 $hr^{-1}$.

17. The process of claim 10 wherein n-butane is converted at about 500° to about 600° C. at a pressure of about 0.3 to about 3 atmospheres with a hydrogen/butane ratio of about 0.5 to about 6 and a weight hourly space velocity of about 1 to about 6 $hr^1$.

18. The process of claim 1 wherein the noble metal is ruthenium, osmium, rhodium, iridium, palladium, platinum or mixtures thereof.

* * * * *